(12) United States Patent
Fitzpatrick et al.

(10) Patent No.: US 7,901,446 B2
(45) Date of Patent: Mar. 8, 2011

(54) THIN-WALLED VASCULAR GRAFT

(75) Inventors: Charles Fitzpatrick, Port Glasgow (GB); Tadanori Okubo, Glasgow (GB)

(73) Assignees: Vascutek Limited, Renfrewshire (GB); Terumo KK, Tokyo (JP)

( * ) Notice: Subject to any disclaimer, the term of this patent is extended or adjusted under 35 U.S.C. 154(b) by 1159 days.

(21) Appl. No.: 11/446,540

(22) Filed: Jun. 2, 2006

(65) Prior Publication Data

US 2009/0036969 A1 Feb. 5, 2009

(30) Foreign Application Priority Data

Jun. 4, 2005 (GB) .................................. 0511431.9

(51) Int. Cl.
*A61F 2/06* (2006.01)

(52) U.S. Cl. ...................................... 623/1.13; 623/1.44

(58) Field of Classification Search .................. None
See application file for complete search history.

(56) References Cited

U.S. PATENT DOCUMENTS

| | | | | |
|---|---|---|---|---|
| 3,953,566 A | 4/1976 | Gore | ............................. | 264/288 |
| 4,619,641 A | 10/1986 | Schanzer | ............................ | 604/8 |
| 5,207,960 A | 5/1993 | Moret de Rocheprise | ... | 264/103 |
| 5,904,967 A | 5/1999 | Ezaki et al. | ............... | 428/36.92 |
| 5,972,441 A * | 10/1999 | Campbell et al. | ............ | 428/34.1 |
| 6,120,477 A | 9/2000 | Campbell et al. | ............... | 604/96 |
| 6,428,571 B1 | 8/2002 | Lentz et al. | .................... | 623/1.4 |
| 6,761,700 B2 * | 7/2004 | Sirimanne et al. | ........... | 604/4.01 |
| 2002/0026231 A1 | 2/2002 | Shannon et al. | .............. | 623/1.13 |
| 2003/0017775 A1 * | 1/2003 | Sowinski et al. | .............. | 442/315 |
| 2003/0028240 A1 * | 2/2003 | Nolting et al. | ............... | 623/1.13 |
| 2003/0139806 A1 | 7/2003 | Haverkost et al. | ........... | 623/1.33 |
| 2004/0033364 A1 | 2/2004 | Spiridigliozzi et al. | ... | 428/411.1 |
| 2004/0182511 A1 | 9/2004 | Rakos et al. | ................... | 156/287 |
| 2004/0215337 A1 | 10/2004 | Hain et al. | ..................... | 623/1.44 |
| 2004/0243042 A1 * | 12/2004 | Lipman | .......................... | 602/43 |
| 2007/0066941 A1 * | 3/2007 | Tezuka et al. | ............. | 604/167.01 |
| 2008/0027534 A1 * | 1/2008 | Edwin et al. | ................. | 623/1.44 |

FOREIGN PATENT DOCUMENTS

| | | |
|---|---|---|
| GB | 2068827 | 8/1981 |
| WO | WO 93/05730 | 4/1993 |
| WO | WO 95/05131 | 2/1995 |
| WO | WO 99/07307 | 2/1999 |
| WO | WO 03/103736 | 12/2003 |
| WO | WO 2005/018502 | 3/2005 |
| WO | WO 2006/026725 | 3/2006 |

* cited by examiner

*Primary Examiner* — Corrine M McDermott
*Assistant Examiner* — Rebecca Straszheim
(74) *Attorney, Agent, or Firm* — Drinker Biddle & Reath LLP

(57) ABSTRACT

There is provided a thin-walled self-sealing vascular graft with a first tubular structure formed from ePTFE and having a wall thickness of 0.2 mm or less, and a resealable polymer layer, such as a styrene copolymer, located on one surface of said first tubular structure. A second tubular structure may also be present, so that the resealable polymer layer is disposed between said first and second tubular structure. The second tubular structure is preferably formed from a textile layer but can also be ePTFE. The graft can be used for replacing a defective portion of the vasculature in a patient in need thereof.

26 Claims, No Drawings

THIN-WALLED VASCULAR GRAFT

The present invention relates to a thin-walled vascular graft comprising expanded polytetrafluoroethylene (ePTFE).

Multi-layer vascular grafts are known in the art. Such grafts may include an elastomer layer which provides self-sealing properties to reduce leakage of blood. In order to seal the graft following needle penetration, the elastomer must be impermeable and non-porous. Consequently the elastomer layer also prevents cellular penetration and tissue ingrowth into the graft wall. Grafts having such an impermeable, non-porous elastomer layers also require other layers with a degree of porosity to be present, to allow the graft to be incorporated into the surrounding tissue. Generally a tri-layer structure is preferred, with the elastomer being sandwiched between two porous layers. Such an arrangement allows a degree of tissue ingrowth on both sides of the graft.

For example, Ezaki et al., in U.S. Pat. No. 5,904,967, describes a tri-layer graft wherein the inner layer is porous polyester resin, the middle layer is self-sealing elastomer and the outer layer is a non-woven fabric of olefin elastomer.

A tri-layer structure has also been used in other medical devices. For example, Campbell in U.S. Pat. No. 6,120,477 describes a balloon catheter with a continuous lumen, which is connected to an inflatable balloon at one end. The balloon is made from PTFE film sealed with an elastomeric material.

Expanded polytetrafluoroethylene (ePTFE) is recognised as being of utility in the manufacture of vascular grafts due to its biocompatibility and low thrombogenicity. ePTFE has a microporous structure which consists of small nodes interconnected by microfibrils. The internodal distance (IND) is the space between nodes and is bridged by the fibrils. The IND gives a measure of the degree of tissue ingrowth possible. Thus a high IND indicates high porosity and thus increased opportunity for cell endothelisation and tissue ingrowth. In vascular applications, the ePTFE may be extruded in tubular form to produce a suitable graft.

Schanzer in U.S. Pat. No. 4,619,641 describes a tri-layer graft suitable for dialysis access. In this graft the inner and outer layers are formed from ePTFE produced in tubular form, with a middle layer of silicone elastomer being injected in liquid form therebetween. The Schanzer graft thus possesses a relatively thick layer (at least 1 mm) of elastomer.

Lentz et al., in U.S. Pat. No. 6,428,571 describes a bi- or tri-layer graft having inner and outer tubular layers of ePTFE, wherein the inner layer has an increased porosity relative to the outer layer. An intermediate layer of a resealable polymer may be present between the two ePTFE layers. Lentz teaches that the less porous outer tubular layer has increased strength relative to the inner layer and so exhibits enhanced radial strength and increased suture retention.

Rakos et al., (US 2004/0182511) describes an implantable prosthesis having a textile layer, an expanded polytetrafluoroethylene (ePTFE) layer and an elastomeric bonding agent layer within the ePTFE porous layer, which joins the textile and ePTFE layer to form an integral structure.

However, such multi-layer grafts suffer from the disadvantage of being thicker than grafts of fewer layers. Increased thickness of the graft wall is disadvantageous since it detracts from the handling characteristics of the graft. In particular the flexibility, suppleness and ease of suturing of the graft decreases with increased wall thickness. However, reducing the thickness of each layer—whilst desirable for overall graft handling—poses significant technical difficulties.

If the graft includes a polyester fabric layer, such layers need to exhibit the necessary strength and stability for vascular graft construction. Thin polyester fabric layers do not show the necessary strength and stability and so there is a minimum thickness of layer required.

The self-sealing elastomer layer also needs to retain a minimum thickness in order to retain its sealing function.

Whilst ePTFE is increasingly being selected for use in vascular grafts, the production of tubular ePTFE with very thin walls and satisfactory uniform wall thickness is technically very difficult.

Tubular ePTFE is made by a discontinuous, batch process. After paste extrusion, individual lengths of extrudate are stretched to create the node and fibril expanded structure. This process is difficult for very thin walled tubes. The extrudate is delicate at this stage, difficult to attach to any stretching fixture and easily damaged. Moreover, the requirement to expand each tube individually makes the production process laborious and costly.

We have now found that a self-sealing graft having reduced wall thickness can be produced by forming an ePTFE tube from pre-formed ePTFE tape by sintering. Such a tube can then be used in the production of a multi-layered self-sealing graft.

The process for manufacturing expanded PTFE tape is well established (see, for example U.S. Pat. No. 3,953,566). Unlike tubing, tape can be produced by a continuous process. Briefly, paste extrusion through a slotted die is followed by thickness reduction between calendering rollers. Stretching, to produce the node and fibril structure, is achieved by drawing the tape over heated rollers running at different speeds. The whole process is continuous and so the problem of fixturing is eliminated, and very thin tapes can be made.

Thin ePTFE tapes are already in use as a reinforcement for commercially available ePTFE grafts (Goretex). In such grafts, unsintered tape is wound directly round an ePTFE tube and the two are sintered together by heating above the crystalline melt point. This approach is not applicable to an elastomer sandwich construction as contemplated in the present invention where the bond needs to be between the ePTFE tape and elastomer, not between ePTFE and ePTFE as in the prior art Gortex graft. Furthermore, the temperature required for sintering is in excess of 350° C., and would not be tolerated by the elastomer which typically has a melting point of 120° C.

The same technique has also been used to produce stand-alone thin walled tubes intended for endovascular stent grafts (see, for example, WO 95/05131) of Gore.

Gore (GB 2068827) teaches wrapping ePTFE tape onto a butt jointed tubular substrate, in order to hold the edges of the tubular substrate in proper abutment. The method described is intended to allow production of relatively large tubes, for example having an inner diameter of 20 mm.

Lentz (U.S. Pat. No. 6,428,571) discloses the use of an ePTFE helically wound tape in a multi-layer graft containing elastomer and designed to be self-sealing. However, the tape in this reference is used to reinforce a conventional tubular ePTFE structure in a manner already known for vascular grafts. The tape is in a single layer and the helix has only one hand to its pitch.

None of the prior art documents discussed above teaches the use of thin-walled tubes formed from the helical winding of ePTFE tape with two or more adjacent layers having a different helical pitch to each other into a multi-layer graft containing an elastomeric layer.

The present invention provides a self-sealing graft comprising:
  i) a first tubular structure formed from ePTFE tape helically wound such that adjacent turns of the ePTFE tape overlap, and wherein said tubular structure has a wall thickness of 0.2 mm or less; and ii) a resealable polymer layer located on one surface of said first tubular structure.

In one embodiment, the first tubular structure is formed by wrapping a layer of unsintered ePTFE tape helically such that adjacent turns of the ePTFE tape have sufficient overlap to ensure at least 2 layers of ePTFE is present at any point along the length of the graft. In one embodiment only two layers of tape are present.

In one embodiment, adjacent turns of the ePTFE tape overlap one another by substantially 50% (preferably 50%) of the width of the tape. In this manner, two layers of tape are present along the length of the graft, with the ends of the graft having a single layer either being optionally trimmed off or allowed to remain to assist anastomosis.

Optionally, the tubular structure includes at least two or more adjacent layers wrapped in a different helical angle to each other. The tape is then sintered on the mandrel by heating above the crystalline melt point of the ePTFE. This step fuses the tape into a thin walled tube. After sintering the tube can be removed from the mandrel. The polymer layer can conveniently be applied whilst the first tubular structure is still located on the mandrel, although this may not be essential.

The self-sealing graft produced as described above may be used in a multi-layer graft (for example a tri-layer graft) or may be used alone. Optionally one of the other layers may be a fabric layer, a further self-sealing polymer or an external support member.

In one embodiment the graft has a helical external support member located thereon, for example a polyester, FEP, PTFE or ePTFE beading.

An advantage of the helical tape construction is that it improves the physical properties of the graft, particularly the value (ie. strength) and uniformity of suture retention. Due to the node and fibril structure, ePTFE is highly anisotropic. The force required to pull out a suture from a conventional ePTFE graft depends on the angle relative to the direction of the nodes. By wrapping tape with different handed helices, the nodes are oriented in more than one direction and the anisotropy is reduced.

In a further aspect, the present invention provides a method of forming a self-sealing graft by:
  i) wrapping two or more layers of unsintered ePTFE tape helically such that adjacent turns of the ePTFE tape overlap;
  ii) sintering the layers of tape by heating above the crystalline melting point of ePTFE to form a sintered tubular structure having a wall thickness of 0.2 mm or less; and
  iii) applying a resealable polymer layer on one surface of said sintered tubular structure.

The ePTFE tape used in the present invention will generally be expanded to have uniaxially orientated fibrils since the manufacture of such tape requires the tape to be expanded in a single direction only, so that the fibrils are aligned in a single direction x. However the use of the tape having biaxially orientated fibrils is not excluded, although this option is not preferred. Biaxially expanded ePTFE will be stretched in two (generally perpendicular) directions x, y and the fibrils will be aligned in both of these directions.

In one embodiment at least one layer of ePTFE tape is helically wound around the mandrel at a helical angle of from 5° to 30°.

In one embodiment at least one layer of ePTFE tape is helically wound around the mandrel at a helical angle of from 10° to 15°, for example about 12°.

In one embodiment, the first tubular structure is formed by wrapping a layer of unsintered ePTFE tape helically such that adjacent turns of the ePTFE tape have sufficient overlap to ensure at least 2 layers of ePTFE is present at any point along the length of the graft. In one embodiment only two layers of tape are present.

In one embodiment, adjacent turns of the ePTFE tape overlap one another by substantially 50% (preferably 50%) of the width of the tape. In this manner, two layers of tape are present along the length of the graft, with the ends of the graft having a single layer either being optionally trimmed off or allowed to remain to assist anastomosis.

In one embodiment at least two adjacent layers of ePTFE are wrapped around the mandrel in different helical directions.

It is possible for the tubular structure to be formed from more than two layers of tape. In one embodiment each layer of tape can be wound at a helical angle that is different to its immediately adjacent neighbouring layers. We have found that the use of 2, 3 or 4 layers of tape is sufficient for the production of most tubes, but the presence of additional layers is not excluded. In some embodiments each layer of tape is wound at an angle which is substantially opposite to that of its immediately adjacent neighbouring layers.

In one embodiment the ePTFE tape is helically wound such that adjacent turns of the ePTFE tape overlap one another by substantially 50% of the width of the tape.

In one embodiment it is possible the sintered ePTFE tubular structure is heat bonded to the resealable polymer layer, for example by heating to a temperature of 100 to 150° C. for up to 15 minutes.

In one embodiment the tape used has a cross-sectional thickness of 0.2 mm or less, for example 0.1 m or less. Generally thin tapes are preferred such as 50 μm or less.

An ePTFE layer constructed from tape in this way enables production of an ePTFE tube having a thin wall thickness. A tube made from tape can have a wall thickness as low as 0.05 mm. Typically such a tube will have a wall thickness of 0.8 mm to 1.2 mm. Preferably, the tube can have a wall thickness of 0.8 mm or less, for example about 0.1 mm. By comparison, ePTFE tubes formed by the conventional methodology of extruding in tubular form and stretching the tube have a typical wall thickness of about 0.4 mm. Even the thinnest available ePTFE tubular grafts formed in this way have a wall thickness of more than 0.2 mm.

The resealable polymer layer is preferably an elastomer. For example the resealable polymer layer may be a thermoplastic elastomer, a silicone or silicone rubber, a polyurethane, polyether, polyester, polyamide, or co-polymers thereof. Conveniently the resealable polymer layer is a styrene copolymer for example is styrene ethylene propylene styrene copolymer (SEPs).

The resealable polymer layer may be applied as a sheet, tape, tube, thread or yarn. Alternatively the resealable polymer layer can be applied as a solution and either dipped, sprayed, painted or extruded onto the first tubular layer. The elastomer may also be applied by injection moulding. In one embodiment, the resealable polymer layer is a tube (i.e. is produced in tubular form before being placed over the sintered tubular structure).

The resealable polymer layer can be disposed between said first tubular structure and a second tubular structure to form a three-layered vascular graft.

In one embodiment the self-sealing polymer is attached to the ePTFE tubular layer by adhesive bonding. Alternatively, if the elastomer is thermoplastic, the bonding may be achieved thermally. In this embodiment the thin-walled ePTFE tube is applied to the outer surface of the elastomer layer and the combination is heated above the melt point of the elastomer. This causes the elastomer layers to fuse together. Optionally, heat-shrinkable tubing may be used to apply an inwards force to the ePTFE layer during the bonding process. Heating at temperatures of 100 to 150° C. for up to 15 minutes (typically 120 to 130° C. for 5 minutes) is usually sufficient to achieve a good bond between the thermoplastic elastomer and ePTFE. In one aspect, the present invention provides a graft as described above further including a second tubular structure. Generally the resealable polymer layer will be sandwiched between the first and second tubular layers.

The second tubular structure may be ePTFE, knitted or woven polyester, or any other suitable graft material. Optionally the second tubular structure may be formed from ePTFE tape as described above for the first tubular structure. Conveniently, the ePTFE may be wound onto a mandrel, which may optionally have the resealable polymer coated first tubular structure already mounted thereon. Alternatively the second tubular structure can be formed independently and then incorporated into the graft.

In one embodiment, the second tubular structure includes at least two adjacent layers of ePTFE tape wrapped in a different helical angle to each other. In one such embodiment, the at least two adjacent layers of ePTFE are wrapped in substantially opposite helical directions.

The tape derived, thin wall tubing may be used as one or more layers of a multi-layer graft, in which one layer is an elastomer layer. It may form either the inner or outer layer, or both.

The resealable polymer may be adhered to the surface of one or both of the tubular structures by any suitable means, and mention may be made of chemical adhesives, heat bonding or mechanical means. The same method of adhesion need not be used for both sides of the polymer layer, ie. the polymer layer can be adhered to the first and second tubular layers by two different methods.

The graft of the present invention may be used as a vascular access graft. In this embodiment the graft self-seals following puncture by a penetrating medical device (for example a hypodermic needle or cannula) accessing the bloodstream of the patient. Multiple puncture is contemplated without loss in self-sealing properties. Consequently the graft can be used to deliver drugs intravenously (for example insulin, chemotherapy drugs, antibiotics and the like) to enable frequent blood samples to be taken from a patient or for dialysis. The graft could also be used for other purposes and the above list is not intended to be exhaustive. Optionally the graft may be implantable into a patient, for example as an AV-fistula.

The graft of the present invention can thus be used to treat a patient by replacing defective portions of the patient's vascular system. Likewise the graft of the present invention can be used in a method of improving vascular access and well as improved drug delivery.

Optionally the graft according to the present invention can be crimped (for example to have a crimp pitch of 2 to 6 mm in the finished graft, for example 2 to 4 mm) or can include a helically wound reinforcing member which is typically a beading of PTFE, ePTFE or fluorinated ethylene propylene (FEP). The reinforcing member is normally adhered to the outer surface of the graft by heat bonding or sintering although chemical adhesion is also possible. The helically wound reinforcing member, which is usually located on the exterior of the graft, enables the graft to be curved without kinking or indenting.

The present invention will now be further described with reference to the following, non-limiting examples.

EXAMPLE 1

Planar woven polyester fabric (29 picks/cm) having a width of 52 mm (ie. to give a diameter of 34 mm when formed into a tube) was placed around a 26 mm diameter mandrel. The fabric was cable-tied onto the mandrel before being placed into an autoclave and heated to 130 to 140° C. to allow the fabric to be heat-set into tubular form. The tubular grafts were allowed to cool so that they became loose on the mandrel, having an approximate diameter of 28 mm.

The grafts were then placed onto a 28 mm diameter mandrel and any creases were smoothed out. A pre-formed 26 mm diameter tubular membrane (0.23 mm thickness) of SEPs was located on top of the tubular fabric layer using a vacuum tube, and a 30 mm diameter pre-formed ePTFE tube was placed on top of the SEPs membrane. The ePTFE was stretched and taped to the mandrel and the whole assembly was heated at 110° C. for 30 minutes to produce the graft of the invention.

An optional crimp step may then be carried out. The cooled graft produced as described above is located onto a 26 mm diameter mandrel and crimped using conventional technologies at a crimp setting to give a pitch of 5 mm. The graft was stretched by 10% prior to heat setting at 130° C. for 20 mins. The grafts were then stretched to a finished crimp size of 3 mm pitch, clipped to the mandrel and heated at 90° C. for 15 minutes. The crimp pitch in the relaxed finished graft was approximately 3 mm.

The example can be repeated using an inner woven fabric large enough to give a diameter of up to 41 mm.

Further, an ePTFE tube of larger diameter (eg. up to 35 mm) can be used.

The graft of Example 1 was subjected to a bend radius test. The graft has a bend radius of less than 10 mm.

EXAMPLE 2

Planar woven polyester fabric (29 picks/cm) having a width of 57 mm (ie. to give a diameter of 36 mm when formed into a tube) was placed around a 26 mm diameter mandrel. The fabric was cable-tied onto the mandrel before being placed into an autoclave and heated to 130 to 140° C. to allow the fabric to be heat-set into tubular form. The tubular grafts were allowed to cool so that they became loose on the mandrel, having an approximate diameter of 28 mm.

The grafts were then placed onto a 28 mm diameter mandrel and any creases were smoothed out. A pre-formed 26 mm diameter tubular membrane (0.23 mm thickness) of SEPs was located on top of the fabric using a vacuum tube, and a 30 mm diameter pre-formed ePTFE tube was placed on top of the SEPs membrane. The ePTFE was stretched and taped to the mandrel and the whole assembly was heated at 110° C. for 30 minutes to produce the graft of the invention.

An optional crimp step may then be carried out. The cooled graft produced as described above is located onto a 26 mm diameter mandrel and crimped using conventional technologies at a crimp setting to give a pitch of 5 mm. The graft was stretched by 10% prior to heat setting at 130° C. for 20 mins. The grafts were then stretched to a finished crimp size of 3 mm pitch, clipped to the mandrel and heated at 90° C. for 15 minutes. The crimp pitch in the relaxed finished graft was approximately 3 mm.

The graft of Example 2 was subjected to a bend radius test. The graft had a bend radius of 10 mm which is satisfactory.

Additionally, the graft of Example 2 was subjected to a water pressure test by being securely attached to a water supply at one end with the other end of the graft being clamped closed. The amount of water leaking from the graft was measured over a one minute period (ignoring any water leaking from the clamped ends). The graft was stretched fully and the test was repeated. The graft was then stretched fully again and the test repeated once more.

For three grafts made according to Example 2 the results are as follows:

|        | Amount of Water (g) |          |          |
| ------ | ------------------- | -------- | -------- |
| Sample | 1st Test            | 2nd Test | 3rd Test |
| 1      | 0                   | 0        | 0        |
| 2      | 0                   | 0        | 0        |
| 3      | 0                   | 1.9      | 4.0      |

In all samples the amount of water leaking was acceptable.

EXAMPLE 3

An unsintered ePTFE tape of 50 μm thickness was wound around a mandrel at a helical pitch of 12 to 15°. A second layer of the same tape was then wound over that first layer in a substantially opposite helical pitch. The graft was sintered at a temperature above the crystalline melting point of ePTFE to produce an ePTFE graft. This graft could be used in Examples 1 and 2.

EXAMPLE 4

An unsintered ePTFE tape of 50 μm thickness was wound onto a mandrel at a helical pitch of 12 to 15°. The tape was wound so that each turn of the tape overlapped the previous turn by half. The graft was sintered at a temperature above the crystalline melting point of ePTFE to produce an ePTFE tube. This ePTFE tube could be used in Examples 1 and 2.

The invention claimed is:

1. A self-sealing graft comprising:
   i) a first tubular structure formed from ePTFE tape helically wound such that adjacent turns of the ePTFE tape overlap and wherein said tubular structure has a wall thickness of 0.2 mm or less;
   ii) a second tubular structure formed from ePTFE by:
      (a) wrapping a layer of unsintered ePTFE tape helically around a mandrel such that adjacent turns of the ePTFE tape overlap, at least two adjacent layers of the ePTFE tape wrapped in a different helical angle to each other;
      (b) sintering the tape by heating above the crystalline melting point of ePTFE to form a sintered tubular structure; and
      (c) removing the sintered ePTFE tubular structure from the mandrel; and
   iii) a resealable polymer layer disposed between said first tubular structure and said second tubular structure.

2. The graft as claimed in claim 1 wherein the first tubular structure has a wall thickness of 0.1 mm or less.

3. The graft as claimed in claim 1 wherein the adjacent turns of the ePTFE tape overlap one another by substantially 50% of the width of the tape.

4. The graft as claimed in claim 1 wherein the first tubular structure is formed by:
   i) wrapping a layer of unsintered ePTFE tape helically around a mandrel such that adjacent turns of the ePTFE tape overlap;
   ii) sintering the tape by heating above the crystalline melting point of ePTFE to form a sintered tubular structure; and
   iii) removing the sintered ePTFE tubular structure from the mandrel.

5. The graft as claimed in claim 4 wherein the first tubular structure includes at least two or more adjacent layers of the ePTFE tape wrapped in a different helical angle to each other.

6. The graft as claimed in claim 5 wherein the two or more layers of the ePTFE tape have substantially opposite helical directions.

7. The graft as claimed in claim 1 wherein said first tubular structure forms an outer layer of said graft.

8. The graft as claimed in claim 1 wherein said first tubular structure forms an inner layer of said graft.

9. The graft as claimed in claim 1 wherein said resealable polymer is a styrene polymer.

10. The graft as claimed in claim 1 wherein said resealable polymer comprising a styrene ethylene propylene styrene copolymer (SEPs).

11. The graft as claimed in claim 1 wherein the at least two adjacent layers of the ePTFE tape of the second tubular structure are wrapped in substantially opposite helical directions.

12. The graft as claimed in claim 1 having a helical external support member located thereon.

13. The graft as claimed in 1 wherein adjacent turns of the ePTFE tape forming the second tubular structure overlap one another by substantially 50% of the width of the tape.

14. A method of treatment of a patient having a defective vascular system, said method comprising replacing a defective portion of the patient's vascular system with the graft as claimed in claim 1.

15. A method of surgery to alleviate a defective portion of the vascular system in a patient in need thereof, said method comprising inserting the graft as claimed in claim 1 into the vascular system of the patient.

16. A method of improving vascular access in a patient in need thereof, said method comprising inserting the graft as claimed in claim 1 into the vascular system of a patient in a position suitable for repeat vascular access.

17. A self-sealing graft comprising:
   (i) a first tubular structure formed from ePTFE tape helically wound such that adjacent turns of the ePTFE tape overlap and wherein said first tubular structure has a wall thickness of 0.2 mm or less;
   (ii) a resealable polymer layer located on one surface of said first tubular structure, said resealable polymer comprising a styrene ethylene propylene styrene copolymer.

18. The graft as claimed in claim 17 wherein the first tubular structure includes at least two or more adjacent layers of the ePTFE tape wrapped in a different helical angle to each other.

19. The graft as claimed in claim 18 wherein the two or more layers of the ePTFE tape have substantially opposite helical directions.

20. A graft as claimed in claim 17 having a second tubular structure, wherein said resealable polymer layer is disposed between said first tubular structure and the second tubular structure.

21. The graft as claimed in claim 19 wherein the second tubular structure is formed from ePTFE.

22. The graft as claimed in claim 21 wherein the second tubular structure is formed by:
   i) wrapping a layer of unsintered ePTFE tape helically around a mandrel such that adjacent turns of the ePTFE tape overlap;
   ii) sintering the tape by heating above the crystalline melting point of ePTFE to form a sintered tubular structure; and
   iii) removing the sintered ePTFE tubular structure from the mandrel, and wherein the second tubular structure includes at least two adjacent layers of the ePTFE tape wrapped in a different helical angle to each other.

23. The graft as claimed in claim 22 wherein the at least two adjacent layers of the ePTFE tape of the second tubular structure are wrapped in substantially opposite helical directions.

24. A method of treatment of a patient having a defective vascular system, said method comprising replacing a defective portion of the patient's vascular system with the graft as claimed in claim 17.

25. A method of surgery to alleviate a defective portion of the vascular system in a patient in need thereof, said method comprising inserting the graft as claimed in claim 17 into the vascular system of the patient.

26. A method of improving vascular access in a patient in need thereof, said method comprising inserting the graft as claimed in claim 17 into the vascular system of a patient in a position suitable for repeat vascular access.

* * * * *

UNITED STATES PATENT AND TRADEMARK OFFICE
CERTIFICATE OF CORRECTION

| | | |
|---|---|---|
| PATENT NO. | : 7,901,446 B2 | Page 1 of 1 |
| APPLICATION NO. | : 11/446540 | |
| DATED | : March 8, 2011 | |
| INVENTOR(S) | : Charles Fitzpatrick and Tadanori Okubo | |

It is certified that error appears in the above-identified patent and that said Letters Patent is hereby corrected as shown below:

Column 7:

line 38, insert --first-- after "said";

Column 8:

line 56, "19" should read --20--.

Signed and Sealed this
Thirty-first Day of May, 2011

David J. Kappos
*Director of the United States Patent and Trademark Office*